United States Patent [19]
Tone

[11] Patent Number: 5,618,736
[45] Date of Patent: Apr. 8, 1997

[54] METHOD FOR USING SYNTHESIZED KAOLINITE AS CARRIER FOR BIOREACTOR, A COMPOSITE BODY COMPOSED SUBSTANTIALLY OF SYNTHESIZED KAOLINITE AS CARRIER AND ENZYME CARRIED ON SYNTHESIZED KAOLINITE, AND BIOREACTOR SYSTEM USING SUCH A COMPOSITE BODY

[75] Inventor: Kisato Tone, Nagoya, Japan

[73] Assignee: NGK Insulators, Ltd., Japan

[21] Appl. No.: 262,506

[22] Filed: Jun. 20, 1994

[30] Foreign Application Priority Data

Jun. 18, 1993 [JP] Japan .................. 5-147584

[51] Int. Cl.⁶ .......................... G01N 33/552
[52] U.S. Cl. .................. 436/527; 435/14; 435/21; 435/27; 435/174; 435/176; 435/182; 435/299.1; 435/299.2
[58] Field of Search ............... 435/14, 174, 176, 435/181, 182, 297.1, 299.1, 299.2, 21, 27; 436/527

[56] References Cited

U.S. PATENT DOCUMENTS

| | | | |
|---|---|---|---|
| 4,338,398 | 7/1982 | Yoneyama | 435/95 |
| 4,560,660 | 12/1985 | Geirnaert | 435/176 |
| 4,572,897 | 2/1986 | Amotz et al. | 435/177 |

FOREIGN PATENT DOCUMENTS

| | | |
|---|---|---|
| 0067459 | 12/1982 | European Pat. Off. . |
| 0118588 | 9/1984 | European Pat. Off. . |
| 4020406 | 1/1992 | Germany . |

OTHER PUBLICATIONS

Database WPI, Section Ch, Week 7845, Derwent Publications Ltd., London, GB; Class D16, AN 78–80941A & JP-A-53 113 082 (Agency of Ind Sci Tech) 3 Oct. 1978.

Database WPI, Section Ch, Week 9026, Derwent Publications Ltd., London, GB; Class D16, AN 90–198025 & JP-A-2 131 578 (Kohjin KK) 21 May 1990.

Database WPI, Section Ch, Week 9026, Derwent Publications Ltd., London, GB; Class B07, AN 91–183100 & JP-A-3 112 808 (Agency of Ind Sci Tech) 14 May 1991.

International Biotechnology Laboratory, vol. 6, No. 3, 1988, Shelton US, pp. 22–27, Adams J.M. et al. "A range of ceramic biosupports".

Clays and Clay Materials, vol. 33, No. 3, 1985, Japan, pp. 200–206, Tomura, Shinji et al. "Growth conditions and genesis of spherical and platy kaolinite".

Primary Examiner—David A. Redding
Attorney, Agent, or Firm—Parkhurst, Wendel & Burr, L.L.P.

[57] ABSTRACT

A process using hydrothermally synthesized porous kaolinite as a carrier for use in a bioreactor. A carrier-biocatalyst composite body for use in a bioreactor, includes the synthesized kaolinite as a carrier and a biocatalyst fixed onto the synthesized kaoline. A bioreactor system includes a bioreactor vessel, and such a carrier-biocatalyst composite body placed in the bioreactor vessel.

35 Claims, 1 Drawing Sheet

5,618,736

METHOD FOR USING SYNTHESIZED KAOLINITE AS CARRIER FOR BIOREACTOR, A COMPOSITE BODY COMPOSED SUBSTANTIALLY OF SYNTHESIZED KAOLINITE AS CARRIER AND ENZYME CARRIED ON SYNTHESIZED KAOLINITE, AND BIOREACTOR SYSTEM USING SUCH A COMPOSITE BODY

BACKGROUND OF THE INVENTION (1) Field of the Invention

The present invention is directed to a method for using a bioreactor carrier to be charged into a bioreactor and adapted to carry a biocatalyst such as an enzyme. More particularly, the invention relates to a method for using hydrothermally synthesized kaolinite as a carrier in a bioreactor, a bioreactor carrier-biocatalyst composite body composed substantially of hydrothermally synthesized kaolinite as a carrier and enzyme carried on the kaolinite carrier, and a bioreactor system using such a composite body.

(2) Related Art Statement

It has been known for a long time that enzymes are adsorbed on synthesized macromolecular materials or enzymes are enclosed and fixed by gels in order to industrially effect bioreaction by using the enzymes. Since these carriers are organic materials, they unfavorably have low strength, and are unsuitable when it is necessary to increase the size of the carrier. For this reason, it has been common in recent times to use purified inorganic minerals, such as silica and alumina, as carriers.

However, for example, when silica is used as a carrier, there is a problem that since silica is likely to be damaged with alkali, it cannot be used over a wide pH range. When alumina is used as a carrier, there is a problem that an amount of an enzyme fixed on the carrier cannot be increased. Further, when a natural inorganic mineral is used as a carrier, such a mineral inevitably contains impurities. Consequently, it is feared that ions such as $Ca^{++}$ and $K+$, which the enzyme dislikes, dissolve out, and thus the activity of the fixed enzyme is deteriorated.

SUMMARY OF THE INVENTION

It is an object of the present invention to solve the above-mentioned problems, and the invention has been accomplished to provide a bioreactor carrier which can be stably used over the entire pH range, has a large capacity of fixing an enzyme thereon, and does not dissolve out impurities which may deteriorate the activity of the enzyme.

More particularly, the invention relates to a method for using hydrothermally synthesized kaolinite as the bioreactor carrier in a bioreactor, a bioreactor carrier-biocatalyst composite body composed substantially of synthesized kaolinite as the carrier and enzyme carried on the kaolinite carrier, and a bioreactor system using such a composite.

The bioreactor carrier according to the present invention, which is to solve the above-mentioned problem, comprises hydrothermally synthesized porous kaolinite.

The hydrothermally synthesized porous kaolinite may be in the form of a honeycomb structural body, a cylindrical body, a rod shape, a planar shape, a block shape, pellets, or granules, and the synthesized kaolinite may be produced in any appropriate form by using a conventional process such as molding, casting, extruding, pressing on granulating.

The invention also relates to a bioreactor carrier-biocatalyst composite body composed substantially of hydrothermally synthesized kaolinite as a carrier and enzyme carried on the kaolinite carrier, and a bioreactor system using such a composite body.

Further, the invention relates to a bioreactor system including a bioreactor vessel and such a bioreactor carrier-biocatalyst composite body placed in the bioreactor vessel. For example, the bioreactor carrier-biocatalyst composite body may be formed by placing the carrier inside the bioreactor vessel and passing a liquid, such as glucoside, containing the biocatalyst through the carrier.

According to the present invention, the following are considered preferable.

(1) The hydrothermally synthesized kaolinite has a pore diameter distribution with at least a peak of fine pores in a range of 400 Å to 600 Å.

(2) The average particle size of the crystals of the hydrothermally synthesized kaolinite is 0.1 μm to 0.5 μm.

(3) The volume percentage of pores having diameters falling in the range of 400 Å–600 Å per the total volume of pores of the hydrothermally synthesized kaolinite is not less than 40%, more preferably 40%–70%. The total volume (cc/g) of the pores falling in the pore sizes of 400–600 is 0.45 cc/g, more preferably 0.45 cc/g–0.55 cc/g.

These and other objects, features and advantages of the invention will be appreciated upon reading of the following description of the invention when taken in conjunction with the attached drawings with the understanding that some modifications, variations and changes of the same could be easily made by the skilled person in the art to which the invention pertains.

BRIEF DESCRIPTION OF THE DRAWING

For a better understanding of the invention, reference is made to the attached drawing, wherein.

DETAILED DESCRIPTION OF THE INVENTION

Figure 1:
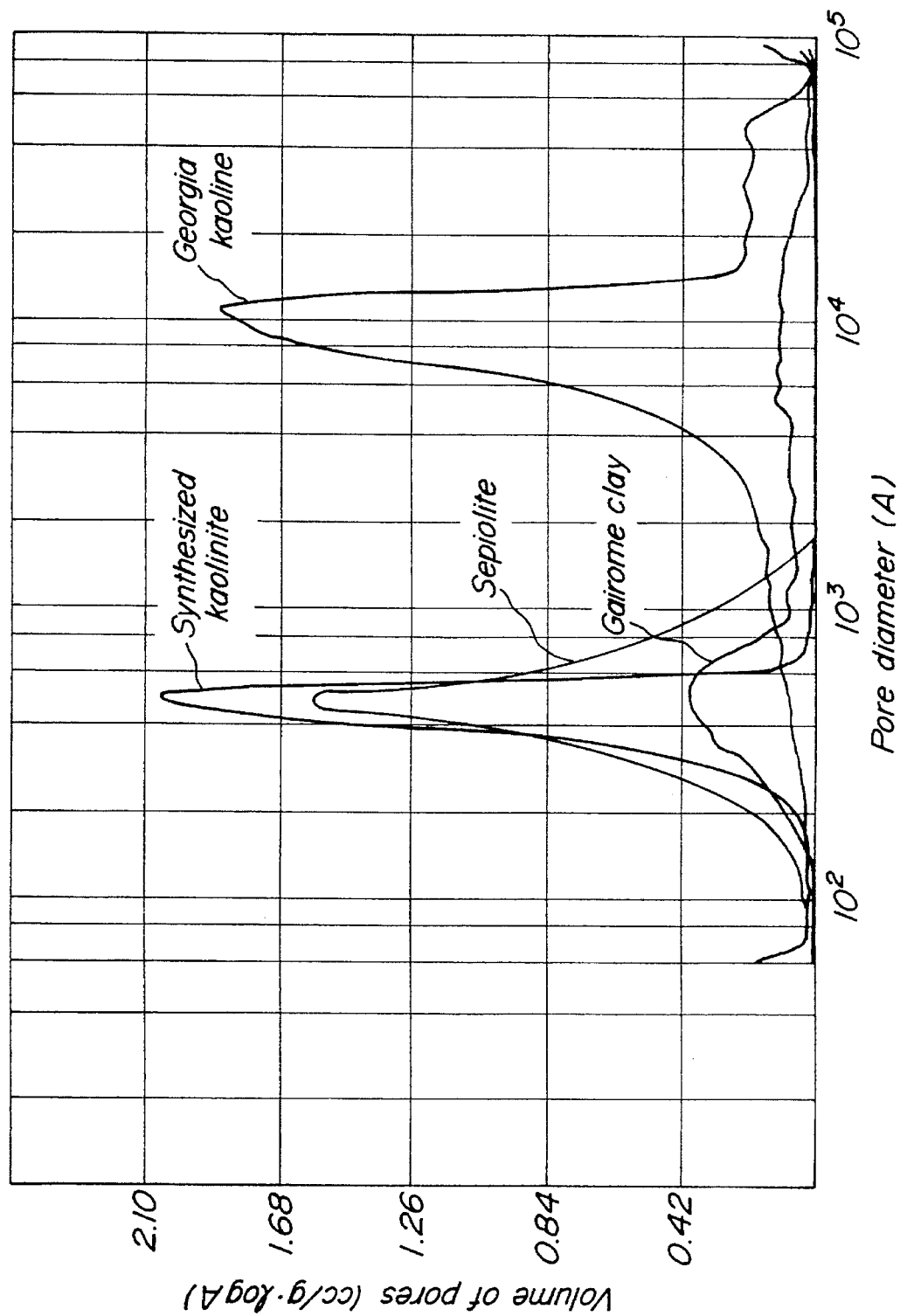
FIG. 1 is a graph showing a fine pore diameter distribution of a synthesized kaolinite as a bioreactor carrier used as an example of the invention together with those of Gairome clay and Georgia kaoline.

As the synthesized kaolinite used in the present invention, a commercial product may be employed, or kaolinite synthesized through hydrothermal crystallization by heating a mixed fine powder of $SiO_2$ and $Al_2O_3$ in an acidic solution may be employed. For example, see Gastuche, M.C., and La Iglesia. A "Clays and Clay Materials", 26,409 (1978), and S. Tomura, Y. Shibasaki and H. Mizuta "Clays and Clay Materials", Vol. 33, pp200–206 (1985).

For example, when the synthesized kaolinite is used in the granular form, the synthesized kaolinite is granulated by preparing a slurry of a hydrothermally synthesized kaolinite and then spray drying the slurry in a spray dryer. The particle diameters of the granules are not limited to any range, but the average particle diameter of the granules is preferably in a range of 10–1000 μm from the standpoint of handling. In order to remove an organic binder added to the slurry in the granulation with the spray dryer, it is preferable to calcine the granules at 650° C.–850° C. for more than 1 hour in an electric furnace. If the calcining temperature is less than 650° C., the strength of the carrier becomes lower, whereas if the calcining temperature is more than 850° C., fine pores cannot be obtained as desired. If the calcining time is less than 1 hour, strength becomes lower. The granules of the resulting synthesized kaolinite are charged in a cylinder, which is set inside a reactor vessel of a bioreactor. It is preferable that a peak exists in a range of 400 Å–600 Å in the pore diameter distribution of the calcined granules. If the pore diameter is less than 400 Å, it is difficult for the enzyme to enter the pore, whereas if it is more than 600 Å, the specific surface area decreases. In either case, the fixed amount of the enzyme decreases. The volume of pores having diameters falling in the range of 400 Å–600 Å per the total volume of the pores of the thus obtained porous kaolinite is preferably not less than 40%.

In the case where the synthesized kaolinite is used in the form of a honeycomb structure, a cylindrical shape, a rod-like shape, a planer shape, or a block-like shape, the kaolinite is shaped by a conventional process such as molding, pressing, extruding, casting or the like. In this case, the above heat treatment may be effected.

The synthesized kaolinite thus prepared is compared with natural kaolinite as follows:

TABLE 1

| | | Natural kaolinite | Synthesized kaolinite |
|---|---|---|---|
| Average face (AB) size | | 10 ~ 0.5 μm | not more than 0.3 μm |
| Chemical analysis (Impurity) | $Fe_2O_3$ | 0.5 ~ 2.0 | not more than 0.2% |
| | $TiO_2$ | 0.8 ~ 1.0 | not more than 0.2% |
| | $CaO$ | 0.18 ~ 0.24 | not more than 0.2% |
| | $MgO$ | 0.35 ~ 0.50 | not more than 0.2% |
| | $K_2O$ | 0.50 ~ 0.70 | not more than 0.1% |
| | $Na_2O$ | 0.09 ~ 1.00 | not more than 0.1% |
| C-face edge thickness (Å) | | 150 ~ 400 | 150 |

As shown by data in examples mentioned later, the thus constituted bioreactor carrier according to the present invention has a number of fine pores having such sizes as suitable for carrying the enzyme, and the amount of the enzyme fixed can be increased up to about two times as much as the conventionally fixed amount. Further, kaolinite has a chemical structure of $Si_2Al_2O_5(OH)_4$, and possesses four OH-groups per one molecule to promote the fixture of the enzyme onto the carrier. Accordingly, the amount of the fixed enzyme can not only be increased, but also the rate of the fixed but peeled enzyme during use can be suppressed to a low level.

Furthermore, since the bioreactor carrier used in the present invention is constituted by hydrothermally synthesized kaolinite, there is no chance of $Ca^{++}$ and $K^+$ dissolution out of the carrier, as in conventional carriers. In addition, since the bioreactor carrier according to the present invention is constituted by hydrothermally synthesized kaolinite, the carrier is resistant to acid and alkali damage, and the carrier can be stably used in the entire pH range. Moreover, the synthesized kaolinite is finer and more uniform than natural kaolinite in that the individual particle size of the crystals of the hydrothermally synthesized kaolinite is ordinarily 0.1–0.5 μm, whereas the minimum particle size of those of natural kaolinite is not less than 0.5 μm. Therefore, the synthesized kaolinite according to the present invention is suitable for fixing the enzyme thereon.

The enzymes which may be carried and fixed onto the bioreactor carrier according to the present invention are not limited to any specific ones, so long as the objects of the present invention can be realized. As the enzymes, α-glucosidase, saccharase, thosphatase, catalase, lipace, and protease may be recited.

As the bioreactor system, ordinary bioreactor equipment may be used. In this bioreactor system, the bioreactor carrier-biocatalyst composite body is placed in a reactor vessel.

EXAMPLES

In the following, examples of the present invention will be explained together with comparative examples.

A slurry having about 30% of water content was prepared by kneading a hydrothermally synthesized kaolinite commercially available under a tradename of TD-series from TOYO DENKA Co., Ltd. together with an organic binder and water, and the slurry was subjected to granulation with a spray dryer. The granular material was calcined at 750° C. for 4 hours to remove the organic binder, thereby obtaining a granular product having an average particle diameter of 70 μm. The specific surface area of the granulate was measured to be 47 $m^2/g$ by the BET method. The pore diameter distribution was determined by the measurement according to the mercury press-in method. As shown in the graph of FIG. 1, a peak is observed in a range of 400 Å–600 Å in the pore diameter distribution.

The granulate obtained above was charged into a cylinder, and an enzyme (α-glucosidase) was fixed onto the granulate as a carrier. Then, an amount of the enzyme per one gram of the carrier, a rate of the enzyme removed from the carrier after a lapse of time of 10–90 minutes since the start of the measurement, an amount of the retained enzyme after the lapse of time of 90 minutes and the activity (U) of glucosidase per one gram of the fixed enzyme were measured. For comparison purposes, needle-shaped silica, commercially available silica, and sepiolite were subjected to the same measurements as given above. The pore diameter distributions of the needle-shaped silica, commercially available silica, and sepiolite are also shown in FIG. 1. Results are shown in Table 2.

The chemical analysis values of the hydrothermally synthesized kaolinite commercially available under a trade name TD from TOYO DENKA Co., Ltd. are as follows:

$SiO_2$: 46–48 wt %
$Al_2O_3$: 36–38 wt %
$Fe_2O_3$: 0.25 wt %
$TiO_2$: ≦0.15 wt %
(Average particle size ≦1 μm)
For Example,

| | |
|---|---|
| Si:47.42 wt %, | CaO:0.19 wt % |
| $Al_2O_3$:37.34 wt %, | $Na_2O$:0.10 wt % |
| $Fe_2O_3$:0.19 wt %, | $K_2O$:0.03 wt % |
| $TiO_2$:0.12 wt %, | |
| MgO:0.14 wt %, | Ig. loss:13.48 wt % |

TABLE 2

| Carrier | Fixed amount of enzyme | Change in peeled-off rate (%) of enzyme with lapse of time | | | | | Amount of remaining enzyme mg/one gram carrier | Activity (U) of glycosidase per one gram enzyme-carried carrier |
| --- | --- | --- | --- | --- | --- | --- | --- | --- |
| | | after 10 minutes | after 20 minutes | after 40 minutes | after 60 minutes | after 90 minutes | | |
| Example (Synthesized kaoline) | 22.1 | 0.47 | 0.80 | 0.86 | 1.43 | 1.49 | 21.8 | 106000 |
| Needle-shaped silica | 11.6 | 11.8 | 13.3 | 15.1 | 15.9 | 17.5 | 9.6 | 40000 |
| Commercially available silica | 12.8 | 19.5 | 19.6 | 19.7 | 20.4 | 20.9 | 10.0 | 58000 |
| Sepiolite | 13.2 | 0.11 | 0.15 | 0.18 | 0.51 | 0.56 | 13.1 | 75000 |

Note: 1U (Activity of glycosidase per one gram enzyme-carried carrier) . . . Amount of enzyme-carried carrier capable of releasing 1 μm of glucose per one hour In the above, the activity of glucosidase was measured as follows:

Ten mM of a buffer solution of acetic acid containing 1 wt % of α-methyl-D-glucoside (adjusted to pH 5 was poured in a total amount of 20 cc into a vessel, and a granular carrier was charged thereinto. Then, 200 mg of the carrier on which was carried the immobilized α-glucosidase was added to the buffer solution. After reacting for 1 hour, an amount of released glucose in 100 μl of the reaction mixture sampled with 100 μl $Na_2Co_3$ was measured by the glucoseoxidase method (For example, see Miwa, I., Okuda, J., Maeda, K. and Okuda, G., "Clin. Chim. Acta." vol. 37, pp 538–540 (1972)).

In this experiment, the total volume (cc/g) of the pores falling in the pore sizes of 400 Å–600 Å was shown together with the percentage of the volume (cc/g) of pores falling in 400–600 per the total pore volume (cc/g).

| | synthesized kaolinite | sepiolite | Gairome clay |
| --- | --- | --- | --- |
| Total volume (cc/g) of the pores falling in the pore sizes of 400Å–600Å | 0.5 | 0.42 | 0.20 |
| Volume (cc/g) of pores falling in 400Å–600Å Total pore volume (cc/g) | 63% | 36% | 27% |

As shown in Table 2, the bioreactor carrier in the above Example had a larger amount of the enzyme fixed thereon, a lower peel-off rate of the enzyme and a larger activity of glucosidase per one gram of the fixed enzyme as compared with the carriers of the Comparative Examples.

As explained above, the bioreactor carrier according to the present invention is composed of hydrothermally synthesized porous kaolinite, and the particle size of the kaolinite is very small. Further, the carrier preferably has a large number of pores having a distribution peak in a range of 400 Å–600 Å as suitable for fixing the enzyme, so that the amount of the enzyme fixed on the carrier is large. In addition, the bioreactor carrier according to the present invention contains substantially no impurities unlike natural kaoline, and does not dissolve out impurities which may damage the activity of the enzyme. Further, the bioreactor carrier can be stably used over the entire pH range, since the carrier is strong against acid and alkaline.

What is claimed is:

1. A method of using porous synthesized kaolinite as a carrier for use in a bioreactor, said synthesized kaolinite being synthesized by hydrothermal crystallization.

2. The method as set forth in claim 1, wherein said synthesized kaolinite is used in a form selected from the group consisting of a honeycomb structure, a cylindrical shape, a rod shape, a planar shape, a block shape, a pellet shape and a granular shape.

3. The method as set forth in claim 1, wherein said synthesized kaolinite has a pore diameter distribution having a peak in a range of 400 Å–600 Å.

4. The method as set forth in claim 3, wherein the volume percentage of pores having diameters falling in the range of 400 Å–600 Å per the total volume of pores of the hydrothermally synthesized kaolinite is not less than 40%.

5. The method as set forth in claim 1, wherein individual particle sizes of crystals of the hydrothermally synthesized kaolinite are 0.1 μm–0.5 μm.

6. The method as set forth in claim 1, wherein the hydrothermally synthesized kaolinite has been calcined at 650° C. to 850° C.

7. A carrier-biocatalyst composite body for use in a bioreactor, said composite body comprising porous synthesized kaolinite as a carrier, and a biocatalyst fixed onto said synthesized kaolinite, said synthesized kaolinite being synthesized by hydrothermal crystallization.

8. The carrier-biocatalyst composite body as set forth in claim 7, wherein said synthesized kaolinite is used in a form selected from the group consisting of a honeycomb structure, a cylindrical shape, a rod shape, a planar shape, a block shape, a pellet shape and a granular shape.

9. The carrier-biocatalyst composite body as set forth in claim 7, wherein said synthesized kaolinite has a pore diameter distribution having a peak in a range of 400 Å–600 Å.

10. The carrier-biocatalyst composite body as set forth in claim 7, wherein said biocatalyst is selected from the group consisting of α-glucosidase, saccarase, phosphotase and catalase.

11. The carrier-biocatalyst composite body as set forth in claim 8, wherein said biocatalyst is selected from the group consisting of α-glucosidase, saccarase, phosphotase and catalase.

12. The carrier-biocatalyst composite body as set forth in claim 7, wherein the volume percentage of pores having diameters falling in the range of 400 Å–600 Å per the total volume of pores of the hydrothermally synthesized kaolinite is not less than 40%.

13. The carrier-biocatalyst composite body as set forth in claim 7, wherein individual particle sizes of crystals of the hydrothermally synthesized kaolinite are 0.1 μm–0.5 μm.

14. The carrier-biocatalyst composite body as set forth in claim 7, wherein the hydrothermally synthesized kaolinite has been calcined at 650° C. to 850° C.

15. A bioreactor system comprising a bioreactor vessel, and a carrier-biocatalyst composite body placed in said bioreactor vessel, said composite body comprising synthesized kaolinite as a carrier, and a biocatalyst fixed onto said synthesized kaolinite, said synthesized kaolinite being synthesized by hydrothermal crystallization.

16. The bioreactor system as set forth in claim 15, wherein said synthesized kaolinite is used in a form selected from the group consisting of a honeycomb structure, a cylindrical shape, a rod shape, a planar shape, a block shape, a pellet shape and a granular shape.

17. The bioreactor system as set forth in claim 9, wherein said kaolinite has a pore diameter distribution having a peak in a range of 400 Å–600 Å.

18. The bioreactor system as set forth in claim 9, wherein said biocatalyst is selected from the group consisting of α-glucosidase, saccharase, phosphatase and catalase.

19. The bioreactor system as set forth in claim 11, wherein said biocatalyst is selected from the group consisting of α-glucosidase, saccharase, phosphatase and catalase.

20. The bioreactor system as set forth in claim 15, wherein the volume percentage of pores having diameters falling in the range of 400 Å–600 Å per the total volume of pores of the hydrothermally synthesized kaolinite is not less than 40%.

21. The bioreactor system as set forth in claim 15, wherein individual particle sizes of crystals of the hydrothermally synthesized kaolinite are 0.1 μm–0.5 μm.

22. The bioreactor system as set forth in claim 15, wherein the hydrothermally synthesized kaolinite has been calcined at 650° C. to 850° C.

23. The method as set forth in claim 2, wherein said synthesized kaolinite has a pore diameter distribution having a peak in a range of 400 Å–600 Å.

24. The method as set forth in claim 2, wherein individual particle sizes of crystals of the hydrothermally synthesized kaolinite are 0.1 μm–0.5 μm.

25. The method as set forth in claim 2, wherein the hydrothermally synthesized kaolinite has been calcined at 650° C. to 850° C.

26. The carrier-biocatalyst composite body as set forth in claim 8, wherein said synthesized kaolinite has a pore diameter distribution having a peak in a range of 400 Å–600 Å.

27. The carrier-biocatalyst composite body as set forth in claim 8, wherein said biocatalyst is selected from the group consisting of α-glucosidase, saccarase, phosphotase and catalase.

28. The carrier-biocatalyst composite body as set forth in claim 8, wherein the volume percentage of pores having diameters falling in the range of 400 Å–600 Å per the total volume of pores of the hydrothermally synthesized kaolinite is not less than 40%.

29. The carrier-biocatalyst composite body as set forth in claim 8, wherein individual particle sizes of crystals of the hydrothermally synthesized kaolinite are 0.1 μm–0.5 μm.

30. The carrier-biocatalyst composite body as set forth in claim 8, wherein the hydrothermally synthesized kaolinite has been calcined at 650° C. to 850° C.

31. The bioreactor system as set forth in claim 10, wherein said kaolinite has a pore diameter distribution having a peak in a range of 400 Å–600 Å.

32. The bioreactor system as set forth in claim 10, wherein said biocatalyst is selected from the group consisting of α-glucosidase, saccarase, phosphatase and catalase.

33. The bioreactor system as set forth in claim 16, wherein the volume percentage of pores having diameters falling in the range of 400 Å–600 Å per the total volume of pores of the hydrothermally synthesized kaolinite is not less than 40%.

34. The bioreactor system as set forth in claim 16, wherein individual particle sizes of crystals of the hydrothermally synthesized kaolinite are 0.1 μm–0.5 μm.

35. The bioreactor system as set forth in claim 16, wherein the hydrothermally synthesized kaolinite has been calcined at 650° C. to 850° C.

\* \* \* \* \*